(12) United States Patent
Barrau et al.

(10) Patent No.: US 11,137,625 B2
(45) Date of Patent: Oct. 5, 2021

(54) METHOD AND OPHTHALMIC ELEMENT FOR STIMULATING A NON-VISUAL PHYSIOLOGICAL EFFECT

(71) Applicant: ESSILOR INTERNATIONAL, Charenton-le-Pont (FR)

(72) Inventors: Coralie Barrau, Charenton-le-Pont (FR); Montserrat Burgos, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 462 days.

(21) Appl. No.: 16/065,270

(22) PCT Filed: Dec. 21, 2016

(86) PCT No.: PCT/EP2016/082214
§ 371 (c)(1),
(2) Date: Jun. 22, 2018

(87) PCT Pub. No.: WO2017/108976
PCT Pub. Date: Jun. 29, 2017

(65) Prior Publication Data
US 2019/0258086 A1 Aug. 22, 2019

(30) Foreign Application Priority Data
Dec. 22, 2015 (EP) .................................. 15307110.5

(51) Int. Cl.
*G02C 3/00* (2006.01)
*G02C 5/00* (2006.01)
(Continued)

(52) U.S. Cl.
CPC .............. *G02C 7/104* (2013.01); *A61F 9/022* (2013.01); *G02C 7/101* (2013.01); *A61F 2002/16965* (2015.04); *G02C 7/102* (2013.01)

(58) Field of Classification Search
CPC ... G02C 7/10; G02C 5/00; G02C 9/00; G02C 7/02; G02C 7/04; G02C 7/08; A61B 3/1005; G02B 5/23
(Continued)

(56) References Cited

U.S. PATENT DOCUMENTS 5,114,218 A 5/1992 Black et al.
6,187,444 B1 2/2001 Bowles, III et al.
(Continued)

FOREIGN PATENT DOCUMENTS

CN 1232977 10/1999
CN 102439512 5/2012
(Continued)

OTHER PUBLICATIONS

Hatori et al., "The emerging roles of melanopsin in behavioral adaptation to light," *Trends in Molecular Medicine*, 2010, 16(10):435-446.
(Continued)

*Primary Examiner* — Dawayne Pinkney
(74) *Attorney, Agent, or Firm* — Norton Rose Fulbright US LLP (57) ABSTRACT

A computed factor allows quantifying the efficiency of a light filter to stimulate a non-visual physiological effect which is responsive to light entering into a subject's eye. The efficiency factor is based on a spectral light transmittance of the filter over the wavelength visible range, on a spectral sensitivity profile of the non-visual physiological effect, and on a spectral distribution of the light which enters into the subject's eye without using the filter. Such efficiency factor is useful in particular for an ophthalmic element designed for stimulating a non-visual physiological effect which is based on melanopsin light-absorption.

12 Claims, 2 Drawing Sheets

(51) Int. Cl.
  *G02C 7/02* (2006.01)
  *G02C 7/10* (2006.01)
  *A61F 9/02* (2006.01)
  *A61F 2/16* (2006.01)

(58) Field of Classification Search
  USPC ....... 351/159.65, 41, 44, 47, 159.01–159.03,
            351/159.39, 159.49, 159.6, 159.61,
                            351/159.73–159.77
  See application file for complete search history.

(56) References Cited

U.S. PATENT DOCUMENTS

| | | |
|---|---|---|
| 7,258,437 B2 | 8/2007 | King et al. |
| 7,520,607 B2 | 4/2009 | Casper et al. |
| 7,748,845 B2 | 7/2010 | Casper et al. |
| 2015/0192800 A1 | 7/2015 | Dirk et al. |

FOREIGN PATENT DOCUMENTS

| | | |
|---|---|---|
| EP | 1866144 | 6/1917 |
| WO | WO 2004/036161 | 4/2004 |
| WO | WO 2010/111499 | 9/2010 |
| WO | WO 2014/011581 | 1/2014 |

OTHER PUBLICATIONS

International Search Report and Written Opinion issued in International Patent Application No. PCT/EP2016/082214, dated Feb. 22, 2017.

METHOD AND OPHTHALMIC ELEMENT FOR STIMULATING A NON-VISUAL PHYSIOLOGICAL EFFECT

CROSS-REFERENCE TO RELATED APPLICATIONS

This application is a national phase application under 35 U.S.C. § 371 of International Application No. PCT/EP2016/082214 filed 21 Dec. 2016, which claims priority to European Patent Application No. 15307110.5 filed 22 Dec. 2015. The entire contents of each of the above-referenced disclosures is specifically incorporated by reference herein without disclaimer.

The invention relates to a method and an ophthalmic element suitable for stimulating a non-visual physiological effect.

BACKGROUND OF THE INVENTION

It has been known for several years that light within the visible range plays a role with respect to non-visual physiological effects for human beings. In particular, part of the visible light participates to regulating circadian rhythms of a subject.

Then, helping to maintain or adapt circadian rhythms may be beneficial for a subject experiencing jet lag or shift work with irregular work periods and rest periods, or sleep troubles. To this purpose, U.S. Pat. No. 7,748,845 proposes method and device for maintaining circadian rhythm in a subject by selectively blocking or reducing retinal exposure to light of wavelengths less than 490 nm (nanometer) during night time. These methods and devices are based on the discovery that the sleep hormone melatonin is affected by light: melatonin secretion is said to be suppressed by nocturnal exposure to light with wavelength between 420 nm and 520 nm.

To the same purpose, U.S. Pat. No. 7,520,607 proposes method and device for inhibiting melatonin suppression by light, by blocking more than 50 percent of incident wavelengths of light having a wavelength range less than, at or about 530 nm, while transmitting more than 50% of non-blocked wavelengths of light. In this way, light-induced suppression of melatonin production can be inhibited when the method and device of U.S. Pat. No. 7,520,607 are implemented at night. In addition, U.S. Pat. No. 7,520,607 discloses that the device used may implement a filter, and may be a user-operable lens, possibly incorporated in an eyewear such as spectacles, goggles, contact lenses and safety glasses.

Starting from this situation, one object of the present invention consists in providing a method for quantifying an efficiency of such device.

Another object of the invention consists in providing a device intended for stimulating a non-visual physiological effect, with a quantified assessment of its efficiency.

SUMMARY OF THE INVENTION

For meeting at least one of these objects or others, a first aspect of the present invention proposes a method for quantifying an efficiency of a light filter with respect to stimulating at least one non-visual physiological effect, this at least one non-visual physiological effect being responsive to part of light entering into a subject's eye. The invention method comprises computing a value of an efficiency factor F for the filter based on a spectral light transmittance T of the filter over the wavelength visible range [380 nm-780 nm] and expressed as percentage values, on a spectral sensitivity profile M of the non-visual physiological effect, and on a spectral distribution E of light intensity corresponding to at least part of the light which enters into the subject's eye without using the filter.

In the frame of the invention, the phrase "stimulating at least one non-visual physiological effect" encompasses any modification of the non-visual physiological effect which is produced by the filter, including triggering, activating, enhancing, reducing, inhibiting and blocking the non-visual physiological effect.

The invention efficiency factor takes into account the spectral features of the filter, and also the spectral features of the non-visual physiological effect and those of the light. Thus, the efficiency factor is a true assessment of the filter efficiency with respect to the non-visual physiological effect in at least one specific light environment.

In preferred implementations of the invention, the efficiency factor F for the filter may be computed using the following formula:

$$F = 100 - \frac{\int_{380nm}^{780nm} E(\lambda) \cdot M(\lambda) \cdot T(\lambda) \cdot d\lambda}{\int_{380nm}^{780nm} E(\lambda) \cdot M(\lambda) \cdot d\lambda} \quad (1)$$

wherein:

$\lambda$ is light wavelength within the visible range from 380 nm to 780 nm;

$T(\lambda)$ is the transmittance value of the filter at wavelength $\lambda$;

$M(\lambda)$ is a value of the spectral sensitivity profile M of the non-visual physiological effect at wavelength $\lambda$; and $E(\lambda)$ is a value of the spectral distribution E of the light intensity at wavelength $\lambda$.

$T(\lambda)$ is expressed as a percentage value, in %, and $E(\lambda)$ may be expressed for example in watt per square meter and per nanometer ($W \cdot m^{-2} \cdot nm^{-1}$). $M(\lambda)$ is expressed as a multiplicative factor applied to the spectral distribution E of the light intensity. In particular, $M(\lambda)$ may be expressed as a percentage value or normalized to unity at maximum value, or using any other scale which is obtained by linear transformation from the percentage M-values. Indeed such linear scale transformations applied to the M-values do not alter the values of the efficiency factor F as resulting from formula (1).

The efficiency factor F is thus based on an average of the filter transmittance T over the wavelength visible range, using products of the values of the spectral sensitivity profile M of the non-visual physiological effect with the values of the spectral distribution E of the light intensity as spectral weighting factors. In addition, the efficiency factor F ranges between 0 and 100 inclusive, and equals 100 for maximum efficiency with respect to the non-visual physiological effect. In particular, the filter may be stated as being efficient for stimulating the at least one non-visual physiological effect if the value of its efficiency factor F is higher than or equal to 30, preferably higher than 70, more preferably higher than 90.

The spectral distribution E of the light intensity may comprise a measured spectral intensity distribution for at least one light source, or a model for a spectral intensity distribution of at least one light source, or a tabulated spectral distribution of the intensity of at least one light source.

In case the light which enters into the subject's eye is a combination of light amounts originating from several light sources, one efficiency factor value may be computed for the filter separately with each light source, using a spectral distribution of the light intensity emitted by this light source. Then, a combined efficiency factor value may be calculated as a weighted average of the efficiency factor values computed respectively with the light sources.

The filter concerned by the invention may be part of an ophthalmic element which is adapted for see-through when used by a wearer equipped with this element. In particular, the filter may be part of an eyeglass, or part of an ophthalmic patch to be fitted on an eyeglass.

When at least two filters are considered, one efficiency factor value may be computed separately for each of these filters, and the method may further comprise comparing the respective efficiency factor values of the filters, and stating the filter which has the highest value for the efficiency factor as being most efficient for stimulating the at least one non-visual physiological effect.

The invention method may further comprise obtaining a value of a b* CIE Lab colorimetric parameter for light transmitted through the filter, and selecting the filter for duplicating or manufacturing several units of this filter if the value of the efficiency factor F is higher than or equal to K×b*, K being a coefficient higher than or equal to 1. The duplicated or manufactured filters then combine aesthetic features, well-rendered colours for the wearer, and efficiency with respect to the non-visual physiological effect. CIE illuminant D65 may be used for assessing the b*-value.

When K-coefficient equals 1.2, b* may be less than 84, in particular for factor F up to 100, or b* may be less than 59, in particular for F factor up to 70, or b* may be less than 25, in particular for F less than or equal to 30.

In particular implementations of the invention, the at least one non-visual physiological effect may be stimulated by reducing a light amount which enters into the subject's eye and which is comprised within a spectral sensitivity range of melanopsin. Then, the spectral sensibility profile M to be used for computing the efficiency factor value may be a spectral sensitivity profile of melanopsin. In such case, the filter may advantageously be designed so that the transmittance T of the filter is less than 70% for at least one first wavelength value comprised in a melanopsin absorption wavelength range limited by a lower limit wavelength and an upper limit wavelength, and the transmittance T of the filter is higher than 70% for at least one second wavelength value which is less than the lower limit wavelength, and higher than 70% also for at least one third wavelength value which is higher than the upper wavelength limit, the first, second and third wavelength values being within the wavelength visible range. Enough light intensity can thus enter into the subject's eye, while maintaining enough efficiency with respect to the non-visual physiological effect.

An improvement for the filters based on the spectral sensitivity profile of melanopsin allows maintaining neutral colour for the light which is transmitted into the subject's eye through the filter. According to this improvement, the filter may be further designed so that its transmittance T has a profile with at least two local-minimum zones and at least one local-maximum zone within the wavelength visible range. A first one of the local-minimum zones contains a local-minimum wavelength which is located within the melanopsin absorption wavelength range, and a second one of the local-minimum zones contains another local-minimum wavelength which is located outside the melanopsin absorption wavelength range, and the local-maximum zone is intermediate in wavelength between said first and second local-minimum zones. Such filter design implements colour-balancing. For such colour-balanced filter, the efficiency factor F may be higher than or equal to K×b*, with K-coefficient possibly higher than or equal to 2.2. The combination of effectiveness with respect to the non-visual physiological effect, good colour rendering for the subject, and colour neutrality or aestheticism of the filtering device is thus highly improved. The second one of the local-minimum zones is preferably shifted towards higher wavelength values with respect to the first local-minimum zone, for melanopsin-based non-visual physiological effect.

In further improved implementations of the invention which are directed to melanopsin-based effects, the second local-minimum zone may overlap at least part of a melanopsin regeneration spectral range, with light having wavelength contained within this melanopsin regeneration spectral range stimulating a regeneration of melanopsin photopigment, in particular a fast regeneration of this latter. Indeed, the invention method and filter use the hypothesis that melanopsin may be bistable. Retinal absorption of radiation with wavelengths comprised between 560 nm to 600 nm, peaking at 580 nm, might be involved in regenerating the melanopsin photopigment. Providing the filter spectral transmittance with two local-minimum zones which are respectively located in the absorption spectral range and in the regeneration spectral range of melanopsin, contributes to an optimized inhibition of melanopsin-containing retinal ganglion cells. Then, the efficiency factor F as defined by formula (1) may be implemented for taking into account such bistable behaviour of melanopsin. To this end, the spectral sensitivity profile M to be used in formula (1) may be a combination of respective spectral sensitivity profiles of two melanopsin states which are involved in melanopsin absorption and melanopsin regeneration. Such profile combination may be a linear combination with appropriate weighting factors.

A second aspect of the invention proposes an ophthalmic element which is adapted for see-through when used by a wearer equipped with this element, and adapted for stimulating at least one non-visual physiological effect. The element has a spectral filtering effect according to a spectral light transmittance T expressed as percentage values over the wavelength visible range [380 nm-780 nm]. It is adapted so that a value of an efficiency factor F which is computed for this element is higher than or equal to 30, preferably higher than 70, more preferably higher than 90, this efficiency factor value being computed based on the transmittance T, on a spectral sensitivity profile M of the non-visual physiological effect, and on a spectral distribution E of light intensity corresponding to at least part of the light which enters into the wearer's eye without using the filter. The efficiency factor value of the element is higher than or equal to K×b*, K being a CIE Lab coefficient higher than or equal to 1, and b* being a colorimetric parameter for the light transmitted through the element. The b*-value may be assessed using the illuminant D65 as defined by CIE.

When K-coefficient equals 1.2, b* may be less than 84, in particular for factor F up to 100, or b* may be less than 59, in particular for F factor up to 70, or b* may be less than 25, in particular for F less than or equal to 30.

Alternatively, K-coefficient may equal 2.2 and b* may be less than 45, preferentially less than 32, and more preferentially less than 14.

In particular, the value of the efficiency factor F may be computed using the above formula (1), where $T(\lambda)$ is the transmittance value of the element at wavelength $\lambda$, expressed as a percentage value, and the other symbols have the meanings already indicated.

The intensity spectral distribution E may relate to daylight, an incandescent light source, an electroluminescent diode, a display backlight, a self-luminous devices or a fluorescent light source.

An integrated light transmission of the element for daylight which is computed over the wavelength visible range may be higher than 70%. In such condition, the element may form a clear eyeglass.

The element may also be a solar protection eyeglass.

The ophthalmic element may be adapted for stimulating a non-visual physiological effect which is based on melanopsin. In such case, the element may advantageously have the features already cited in this concern for a filter.

In preferred embodiments of the invention, the ophthalmic element may comprise a portion of a transparent matrix material, and also a first amount of a first absorber which is distributed within the transparent matrix material. This first absorber may have a first light-absorption maximum which is between 460 nm and 510 nm for the wavelength value of a light impinging on the ophthalmic element. Such wavelength range corresponds to maximum light-absorption by melanopsin. Preferably, the first absorber may be such that the first light-absorption maximum is between 487 nm and 497 nm for the light wavelength with a full width at half maximum of less than 40 nm, when this first absorber is dissolved in methylene chloride ($CH_2Cl_2$).

Most preferably, and in particular for implementing the colour-balancing effect, the ophthalmic element may further comprise a second amount of a second absorber which is also distributed within the transparent matrix material. This second absorber may have a second light-absorption maximum which is between 550 nm and 630 nm for the wavelength value of the light impinging on the ophthalmic element. Such wavelength range corresponds to light-induced melanopsin regeneration. Preferably, the second absorber may be such that the second light-absorption maximum is between 579 nm and 589 nm for the light wavelength with a full width at half maximum of less than 30 nm, when this second absorber is dissolved in methylene chloride.

When such ophthalmic element comprises amounts of both the first absorber and the second absorber, these amounts may be such that the efficiency factor of the ophthalmic element is higher than 30 and b* is less than 10.

The ophthalmic element may also be adapted for remaining in either one of at least two states each corresponding to one value for the efficiency factor F which is distinct from the value relating to the other state, and the element may also be adapted for switching between both states. In the jargon of the Man skilled in the art, the ophthalmic element may thus be a smart element. In particular, the states of the element may be electrically controlled. The element may also further comprise a controller which is adapted for real-time controlling the current state of the element, and controlling a switching to the other state based on at least one of the following criteria:
- at least one feature of the light currently reaching the element;
- an history of at least one feature for the light which has reached the element during a time period;
- the age of the wearer of the element;
- behaviour data and/or lifestyle data of the wearer of the element; and
- at least one control action entered by the wearer of the element.

Generally for the second invention aspect, the ophthalmic element may form at least part of an eyeglass or at least part of an ophthalmic patch to be fitted on an eyeglass.

These and other features of the invention will be now described with reference to the appended figures, which relate to preferred but not-limiting embodiments of the invention.

BRIEF DESCRIPTION OF THE DRAWINGS

For clarity sake, element sizes which appear in FIG. 4 do not correspond to actual dimensions or dimension ratios.

DETAILED DESCRIPTION OF THE INVENTION

Although the invention can be applied to any non-visual physiological effect, it is now described for such effects which are stimulated by melanopsin as an example.

Melanopsin is the third photoreceptor in human retina, recently discovered (~year 2000). This is a natural photopigment, contained in only 1 to 3% of retinal ganglion cells, which generates signals intended to non-visual areas of brain. These signals participate in particular to regulating various non-visual biological functions, including mood, body temperature, pupillary reflex, hormonal behaviours and also features of the biological time of a human being. It is also well-known that sleeping is improved when melatonin hormone is produced, but melatonin production is inhibited by light-stimulation of melanopsin. In some situations, it may be desired to inhibit at least some of the melanopsin-based effects for improving the behaviour of a subject. This may be useful for subjects having irregular or upset rhythms, for example due to jet lag, shift work or prolonged light exposure to self-luminous devices in the evening.

Figure 1:
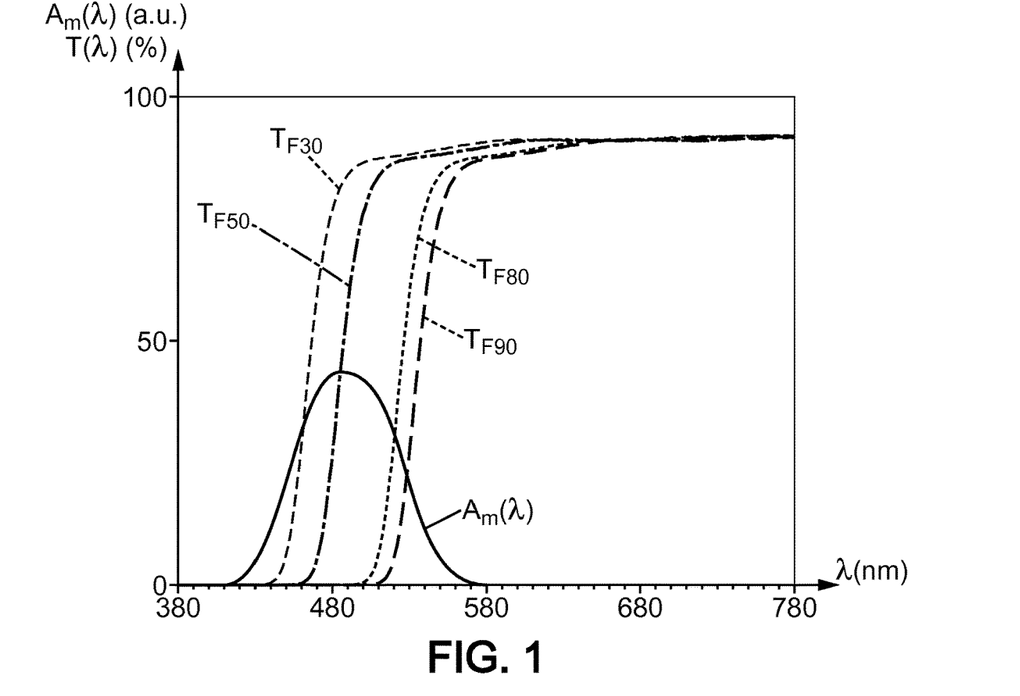
FIGS. 1 to 3 are spectral diagrams for several filters designed by implementing the invention.

Light absorption for melanopsin occurs for light having wavelengths comprised in the range from 410 nm (nanometer) to 580 nm, from 450 nm to 530 nm for half-maximum sensitivity, and from 460 nm to 510 nm for highest sensitivity, as represented in the diagram of claim 1. In this diagram, x-axis represents wavelength values A over the visible range from 380 nm to 780 nm, and y-axis represents the spectral absorption values $A_m(\lambda)$ of melanopsin expressed as percent values of incident light. Therefore, light with wavelengths within this absorption range stimulates melanopsin-based non-visual physiological effects. Exact values of $A_m(\lambda)$ are available in scientific literature.

To this purpose, goggles and spectacles have been proposed which have a light-filtering effect adapted for melanopsin sensitivity spectrum. Such known goggles and spectacles comprise a long-pass absorptive filter with cut-off wavelength from the range 510 nm to 530 nm. Such know goggles and spectacles strongly affect the perception of colour and the scotopic vision, and they are seen as aesthetically displeasing. Indeed, such goggles appear yellow-orange. They have a very high b* value indicating an absence of colour neutrality. In addition, these known goggles and spectacles do not integrate any intermediate efficiency or modulating effect.

Furthermore, it is difficult to determine the efficiencies of several of these devices with respect to melanopsin-based physiological effects since commonly used parameters such as mean light transmission or colorimetric parameters do not match the melanopsin absorption range. For addressing this issue, the present invention introduces the following efficiency factor F:

$$F = 100 - \frac{\int_{380\,nm}^{780\,nm} E(\lambda) \cdot M(\lambda) \cdot T(\lambda) \cdot d\lambda}{\int_{380\,nm}^{780\,nm} E(\lambda) \cdot M(\lambda) \cdot d\lambda} \quad (1)$$

where $E(\lambda)$ is the value at wavelength $\lambda$ of the light intensity distribution E corresponding to incident light entering into the wearer's eye when no goggles or spectacles is worn, expressed in unit $W \cdot m^{-2} \cdot nm^{-1}$, $M(\lambda)$ is the value at wavelength $\lambda$ of the spectral sensitivity profile M of the non-visual physiological effect, expressed as a multiplicative factor applied to the light intensity distribution E, and $T(\lambda)$ is the value at wavelength $\lambda$ of the light transmission of the goggles or spectacles, expressed as a percentage value. In the particular case of a melanopsin-based physiological effect, the spectral absorption values $A_m(\lambda)$ of melanopsin are to be used for the values $M(\lambda)$, possibly expressed as percentage values. The efficiency factor F is then suitable for quantifying the efficiency of the goggles or spectacles for blocking the light components having wavelength values within the absorption range of melanopsin. F equaling 100 means that all light within the absorption range of melanopsin is filtered out by the goggles or spectacles, and F equaling 0 means that the goggles or spectacles have no influence on the melanopsin-based physiological effects. Diagram of FIG. 1 also shows four filter profiles denoted $T_{F30}$, $T_{F50}$, $T_{F80}$ and $T_{F90}$ which correspond respectively to values of about 30, about 50, about 80 and about 90 for the efficiency factor F. Obviously, the invention efficiency factor F may be applied to vision devices other than goggles and spectacles, used only as examples in the present description.

But although the filter profiles $T_{F30}$, $T_{F50}$ and $T_{F80}$ show some efficiency of the related vision devices with respect to the melanopsin-based physiological effects, these devices exhibit intense color in transmission, such that color rendering may be altered for the wearers of these devices. Because the long pass absorptive filters corresponding to the profiles $T_{F30}$, $T_{F50}$ and $T_{F80}$ are designed to reduce or block light when wavelength is below 527 nm, the devices appear yellow or orange in transmission. This transmission colour can be quantified with the well-known b* colorimetric parameter, for example measured or computed for illuminant A or for one illuminant from the series D and F as defined in CIE standard, for example illuminant D65. Practically, designing filters with high values for the efficiency factor F with respect to melanopsin-based physiological effects may lead to high values for b* colorimetric parameter, which are detrimental for colour rendering.

Figure 2:
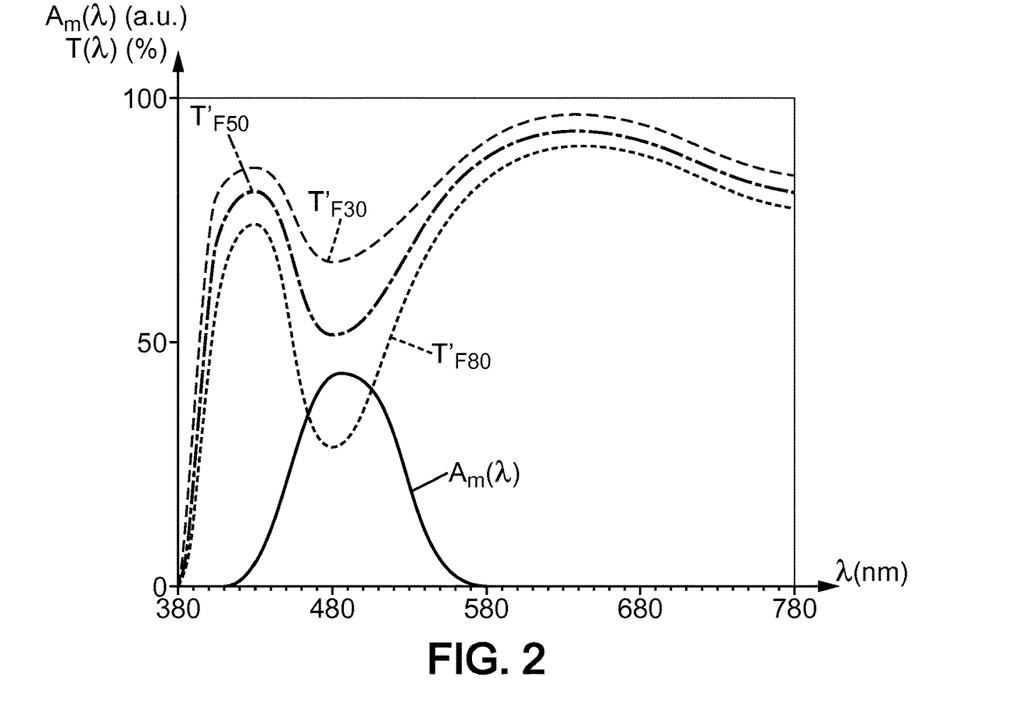
Figure 3:
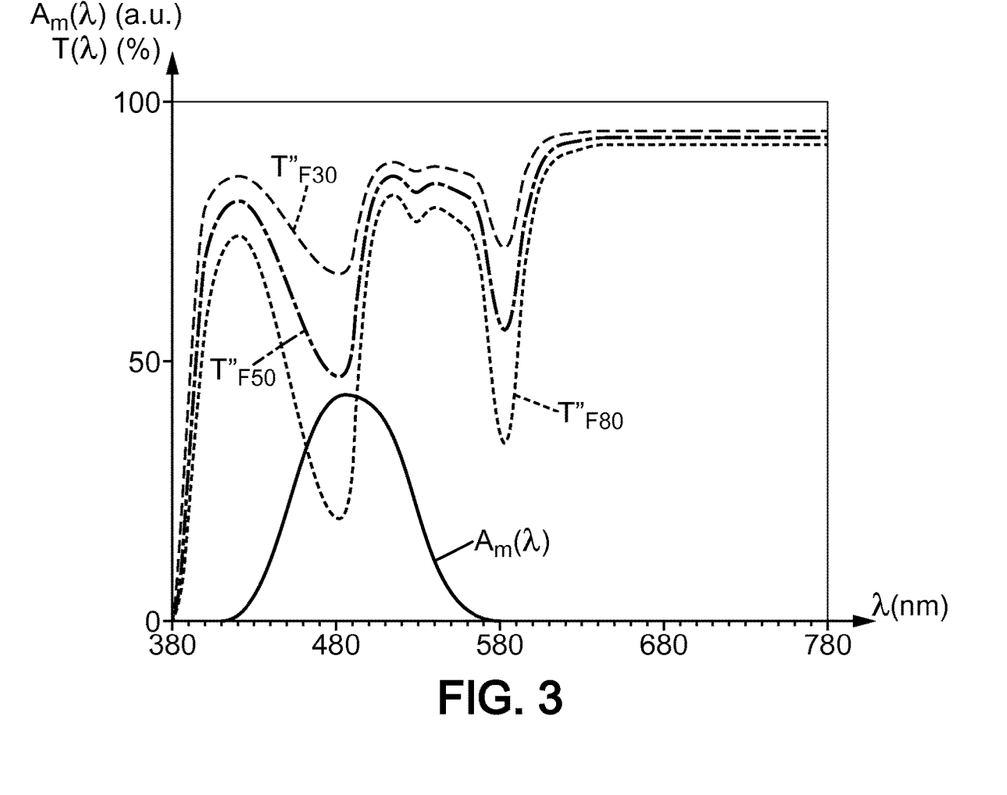

Several ways may be implemented for alleviating this problem of colour rendering, which are now indicated and may be implemented separately or in combination of at least two of them:
  modifying the filter profiles $T_{F30}$, $T_{F50}$ and $T_{F80}$ shown in FIG. 1 so as to obtain new profiles with reduced light transmission values in the melanopsin absorption wavelength range, namely between 460 nm and 510 nm, but with increased light transmission values for at least some wavelength values below 460 nm and at least some other wavelength values above 510 nm. Put another way, the profile may advantageously exhibit a local-minimum zone corresponding to the melanopsin absorption wavelength range, but also two local-maximum zones located below 460 nm and above 510 nm respectively. In this way, the local-maximum zone located below 460 nm tends to lower the value of the b* colorimetric parameter by re-introducing violet light components in the light transmitted by the vision device to the wearer's eye. This may be called a "selectivity effect". Diagram of FIG. 2 is similar to that of FIG. 1 with the melanopsin absorption profile again, but where the additional profiles labelled T'F$_{30}$, T'F$_{50}$ and T'F$_{80}$ corresponds to the second profile type currently described. The profiles T'F$_{30}$, T'F$_{50}$ and T'F$_{80}$ correspond substantially to the same values for the efficiency factor F as the profiles $T_{F30}$, $T_{F50}$ and $T_{F80}$, respectively, since $T_{F30}$ and T'F$_{30}$ have similar values over the melanopsin absorption range as shown in FIGS. 1 and 2, and also for $T_{F50}$ and $T'_{F50}$, and also again for $T_{F80}$ and T'F$_{80}$.
  another way for improving colour rendering of the vision devices without decreasing the efficiency factor values consists in designing the transmission profile of the filter so that it exhibits another local-minimum zone in addition to a first local-minimum zone which is superposed to the melanopsin absorption range. Both local-minimum zones are then separated by a local-maximum zone which may be located just above 520 nm. The second local-minimum zone, above the melanopsin absorption range and the local-maximum zone reduces the contribution of the high wavelength values in the b* colorimetric parameter, thereby reducing the value of this latter. This may be called a "colour-balancing effect". Diagram of FIG. 3 is similar again to that of FIG. 1, but where the additional profiles labelled T"F$_{30}$, T"F$_{50}$ and T"F$_{ao}$ corresponds to the third profile type currently described. The profiles T"$_{30}$, T"$_{50}$ and T"$_{F80}$ also correspond substantially to the same values for the efficiency factor F as the profiles $T_{F30}$, $T_{F50}$ and $T_{F80}$, respectively, for the same reason as already mentioned, when, using again the same spectral absorption profile of melanopsin. Actually, the filter profiles shown in FIG. 3 are combinations of selectivity and colour balancing profile types (second and third profile types). It combines a local-maximum zone below 460 nm, a local-minimum zone in the melanopsin absorption range between 460 nm and 510 nm, another local-maximum zone between 510 nm and 550 nm, and another local-minimum zone between 550 nm and 630 nm.
  selecting a trade-off between stimulating efficiently the melanopsin-based physiological effects and limiting the b* parameter value. Such trade-off may be expressed as the efficiency factor F being higher than or equal to K×b*, where K is a coefficient higher than or equal to 1. Positive feedbacks have been received from wearers using devices with K-coefficient equalling 1.2 and b* being less than 84. Maintaining the trade-off condition of F less than or equal to 1.2×b* with lower values for the b* colorimetric parameter leads to improved vision devices. Preferably, the value of a* colorimetric parameter is positive or zero, for the same illuminant as used for b*.

A special requirement for colour rendering through each filter may be expressed in terms of Q-signal values for automotive driving applications. Known Q-signal requirements may be complied with by the filter, for ensuring that base colours can be identified clearly by a subject through the filter. Each filter in accordance with the invention meets the Q-signal value limitations better than prior art long pass filters profile types which are yellow-orange.

Actually, melanopsin has dual light sensitivity: it absorbs light in the wavelength range 460 nm-510 nm and consequently stimulates non-visual physiological effects as explained before, but also absorbs at about 560 nm-600 nm, mostly 580 nm, for melanopsin regeneration. Indeed, when melanopsin molecules absorb light with wavelength between 460 nm and 510 nm, they are converted from a first molecule state to a second molecule state which is no longer sensitive to light of between 460 nm and 510 nm. But they are then sensitive to light with wavelength comprised between 550 nm and 630 nm which causes them to transform back into the first state. Thus, melanopsin can be regenerated with light in this latter wavelength range. Then, a completed way to inhibit the non-visual physiological effects which are melanopsin-based consists in inhibiting melanopsin regeneration in addition to reducing or suppressing exposure to light which produces stimulation of the non-visual physiological effects. This may be obtained with filter transmission profiles of the third type as disclosed before, by locating the second local-minimum zone at the melanopsin regeneration wavelength range, namely superposing the second local-minimum zone of a filter transmission profile of the third type with wavelength range 550 nm-630 nm. Profiles in FIG. 3 correspond to such implementation. This is called "dual-melanopsin effect" by the inventors.

For rendering in an improved manner such dual-melanopsin effect, the spectral sensitivity profile $M(\lambda)$ to be used for computing the efficiency factor F may be a combination of the respective spectral sensitivity profiles of both molecular states of melanopsin. When linear combination is used, $M(\lambda)=\alpha_1 \cdot M_1(\lambda)+\alpha_2 \cdot M_2(\lambda)$, where $M_1(\lambda)$ is the spectral sensitivity profile of a first one of the molecular states of melanopsin, $M_2(\lambda)$ is the spectral sensitivity profile of a second one of these molecular states of melanopsin, and $\alpha_1$ and $\alpha_2$ are weighting factors. $M_1(\lambda)$ and $M_2(\lambda)$ may be the respective spectral absorption profiles of both melanopsin states, which are known from scientific literature. The spectral absorption profile $M_1(\lambda)$ peaks between 460 nm and 510 nm, and the spectral absorption profile $M_2(\lambda)$ peaks between 550 nm and 630 nm. For example, the weighting factors $\alpha_1$ and $\alpha_2$ may both equal 0.5, or $\alpha_1$ may equal 0.75 and $\alpha_2$ may equal 0.25 as another example.

The light intensity distribution E may be that of any illuminant known in the art. It may also be spectral intensity distribution of any actual light source, for example which is to be used by the wearer of the invention ophthalmic element, including daylight, an incandescent light source, an electroluminescent diode, a display backlight or a fluorescent source. But the light intensity distribution may also be a combination of light amounts originating from several light sources, each one corresponding to a separate light intensity distribution $E_i$, i being a positive integer from 1 to N, where N is the number of sources. In such case, a separate efficiency factor $F_i$ may be computed for one same filter or ophthalmic element but for each light source i, according to the following formula (1'):

$$F_i = 100 - \frac{\int_{380\,nm}^{780\,nm} E_i(\lambda) \cdot M(\lambda) \cdot T(\lambda) \cdot d\lambda}{\int_{380\,nm}^{780\,nm} E_i(\lambda) \cdot M(\lambda) \cdot d\lambda} \quad (1')$$

Then, a combined efficiency factor F may be calculated from these separate efficiency factors $F_i$ by linear combination according to formula (2):

$$F = \frac{1}{N} \sum_{i=1}^{i=N} w_i \cdot F_i \quad (2)$$

where $w_i$ is a weighting factor for light source i. Such averaged efficiency factor F as resulting from formula (2) makes it possible to fit an actual light composition experienced by a subject at one time, or also to fit a light composition which varies between several exposure periods. For the first case, when the actual light originates simultaneously from N light sources, each weighting factor $w_i$ may correspond to the light intensity of the light source i integrated over the visible range, divided by the total light intensity summed over the N light sources, also integrated over the visible range. For the second case where the subject is exposed to different light sources during respective durations, each weighting factor $w_i$ may correspond to the fraction of exposure duration for light source i, divided by the sum of the exposure durations for all N light sources. Each light source i for these multiple exposure situations may be daylight, an incandescent light source, an electroluminescent diode, a display backlight or a fluorescent source independently from the other light sources.

Once the above rules for designing a filter dedicated for stimulating a non-visual physiological effect have been provided, producing such filter comprises selecting appropriately parameters or components of the filter, including die molecules, filter thickness and die concentrations for an absorption-based filter, or including a light-wave propagation medium, thickness of the light-wave propagation medium, interface forming materials or interface layers for a reflection-based filter. Possibly, several filters of various types may be combined by lamination on one another for obtaining a resulting filter profile which matches a target profile designed according to the invention.

Such filter may be self-supported, in particular for a vision device such as eyeglasses, goggles, mask, protection sheet, helmet window, etc. Possibly, it may also be laminated between protective transparent films for reducing scratches and allowing easy cleaning.

Alternatively, the filter may be laminated on a transparent substrate for producing the desired stimulation of the non-visual physiological effect in addition to visual functions provided by the transparent substrate. In particular, the transparent substrate may be an eyeglass lens for ophthalmic applications. Such eyeglass lens may be an ametropia-correcting lens, or a solar protection lens, or a base eyeglass lens dedicated to any other purpose. Possibly, the solar protection function may be provided not only by the substrate, but may result from the combination of the substrate with the filter, or may be provided by the filter only. Also possibly, the filter may form an ophthalmic patch to be applied on an eyeglass.

If several filters are combined, some of them may be laminated on a first face of the substrate, and the other filters may be laminated on a second face of the substrate, opposite the first face. In such case, the filters of both faces may be similar or different.

Each filter may be laminated on a substrate-forming lens, this substrate-forming lens possibly bearing functional layers, by lamination process as taught in EP 1 866 144.

Figure 4:
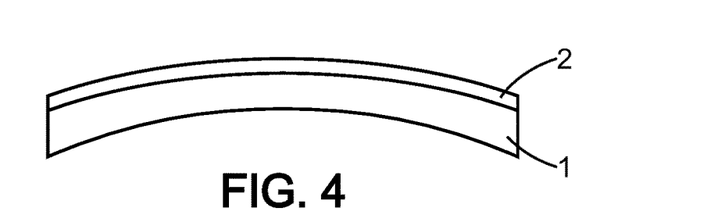
FIG. 4 is a cross-section of an eyeglass in accordance with the invention.

FIG. 4 illustrates an eyeglass obtained by laminating a filter designed according to the invention on a substrate-forming ophthalmic lens. Reference numbers 1 and 2 denote the ophthalmic lens and the filter, respectively.

More specifically, eyeglasses which can be used as substrates may be lenses aimed at correcting the wearer's vision, protecting the wearer's eyes and/or enhancing the wearer's vision. Non-limiting examples of suitable ophthalmic lenses include non-corrective (also called plano or afocal lenses) and corrective lenses, including single vision or multi-vision lenses like bifocal, trifocal or progressive lenses, which may be either segmented or non-segmented. Such ophthalmic lenses may be semi-finished lenses or finished lenses, and in general any type of ophthalmic substrate used in ophthalmic industry, for eyeglasses but also contact lenses. It may be out of mineral glass or organic material.

The organic material for the substrate-forming lens may be a thermoplastic material, selected from polyamides, polyimides, polysulfones, polycarbonates, polyurethanes and copolymers thereof, poly(ethylene terephtalate) and polymethylmethacrylate (PMMA), for instance. As used herein, polycarbonate (PC) is intended to mean either homopolycarbonates or copolycarbonates or block-copolycarbonates. (Co)polymer is intended to mean a copolymer or a polymer, and (meth)acrylate is intended to mean an acrylate or a methacrylate.

The organic material for the substrate-forming lens may be also a thermoset material, selected from cycloolefin copolymers such as ethylene/norbornene or ethylene/cyclopentadiene copolymers, homo- and copolymers of allyl carbonates of linear or branched aliphatic or aromatic polyols, such as homopolymers of diethylene glycol bis(allyl carbonate) (CR 39®), homo- and copolymers of (meth) acrylic acid and esters thereof, which may be derived from bisphenol A, polymers and copolymers of thio(meth)acrylic acid and esters thereof, polymers and copolymers of allyl esters which may be derived from Bisphenol A or phtalic acids and allyl aromatics such as styrene, polymers and copolymers of urethane and thiourethane, and polymers and copolymers of sulphide, disulfide and episulfide, and combinations thereof, for instance.

Particularly recommended substrate-forming lenses include those substrates obtained through (co)polymerization of the diethyleneglycol bis-allyl-carbonate, marketed for example under the trade name CR-39® by the PPG Industries company (ORMA® lenses, ESSILOR), or polythiourethanes/polysulfides, marketed for instance under MR series by Mitsui, or allylic and (meth)acrylic copolymers, having a refractive index between 1.54 and 1.58. Still another organic material which is suitable for the substrate-forming lens is that marketed under trade name Trivex® by PPG Industries company, and which is obtained from nitrogen-enriched urethane-based pre-polymer.

All the materials cited here-above for the substrate-forming lens when the invention filter is supported by such substrate-forming lens, may also be used as filter matrix materials for self-supported filters. In these latter cases, dies molecules may be distributed within the matrix material.

When the filter is supported by a substrate-forming lens, the matrix material of the filter may also be a varnish, or may be a polyurethane-based layer as those described in U.S. Pat. Nos. 6,187,444 and 7,258,437.

A filter which implements the invention may have a single layer or multilayer structure. It may be deposited directly onto the substrate-forming lens. In some applications, the substrate-forming lens is coated with one or more functional coatings prior to depositing the filter. In other applications, one or more functional coatings are coated on the filter. These functional coatings commonly used in optics may be, without limitation, an impact-resistant primer layer, an abrasion-resistant coating and/or a scratch-resistant coating, a polarizing coating, a photochromic coating or a tinted coating. Coatings capable of modifying the surface properties, such as hydrophobic and/or oleophobic coatings (antifouling, antistain, antifog), may also be deposited onto the exposed surface of the last functional coating along a direction away from the substrate.

In particular, coatings may be used in combination with the filter for aesthetic matters, in particular for selecting the colour and intensity of the light-reflection produced by the ophthalmic element from light originating from the wearer's environment, including daylight from sky.

Filters in accordance with the invention, and which are directed to melanopsin-based physiological effects have been produced using one or two absorbers produced by Exciton, Inc. in Dayton, Ohio, US. The first absorber is referred to as P491 and has an absorbance peak at wavelength value of 492+/−1 nm in methylene chloride ($CH_2Cl_2$), corresponding to the absorbance range of melanopsin. Full width at half maximum for the P491 absorbance peak is about 32 nm. The second absorber is referred to as ABS 584L and has an absorbance peak at wavelength value of 584+/−2 nm in methylene chloride, corresponding to the regeneration range of melanopsin. Full width at half maximum for the ABS 584L absorbance peak is about 22 nm.

Three filters have been produced using the following absorber amounts incorporated in one clear substrate material for forming ophthalmic lenses:
- filter F1: 1.2 mg (milligram) of absorber Exciton P491 per 100 g (gram) of clear substrate material, without any Exciton ABS 584L
- filter F2: 1.2 mg (milligram) of absorber Exciton P491 and 0.9 mg of absorber Exciton ABS 584L per 100 g (gram) of clear substrate material
- filter F3: 2.4 mg (milligram) of absorber Exciton P491 per 100 g (gram) of clear substrate material, without any Exciton ABS 584L For comparison, a filter F0 is comprised on the clear substrate material without any absorber. All four filters have one and same thickness value for the measured or assessed features which are displayed in the following table:

|    | TBV(%) | TBT(%) | TA(%) | Tv(%) | b*  | F  | x(%) | y(%) |
|----|--------|--------|-------|-------|-----|----|------|------|
| F1 | 71     | 51     | 97    | 90    | 17  | 27 | 28   | NS   |
| F2 | 73     | 52     | 58    | 77    | 6   | 32 | 62   | 50   |
| F3 | 66     | 34     | 95    | 87    | 23  | 35 | 78   | 50   |
| F0 | 95     | 99     | 98    | 98    | 1.4 | 1  | —    | —    |

TBV: transmission value over the wavelength range 415-455 nm (blue-violet color)
TBT: transmission value over the wavelength range 460-510 nm (blue-turquoise colour)
TA: transmission value over the wavelength range 570-600 nm (amber colour)
Tv: visual transparency over the range 380-780 nm for human eye
b*: colorimetric parameter of CIE Lab model, positive b*-values denoting yellowish hue and negative b*-values denoting bluish hue
F: the invention efficiency factor, computed using the spectral absorption profiles $M_1(\lambda)$ and $M_2(\lambda)$ of both molecular states of melanopsin, $M_1(\lambda)$ peaking between 460 nm and 510 nm, and $M_2(\lambda)$ peaking between 550 nm and 630 nm, and the following weighting factors for the linear combination: $\alpha_1 = 0.75$ and $\alpha_2 = 0.25$
x: the increase in melatonin production with respect to the filter F0
y: the decrease in sleep latency with respect to the filter F0

In this table, the column features are the following ones when calculated for the illuminant D65 of CIE:

The three filters F1 to F3 implement the selectivity effect previously described, and the higher value of the efficiency factor for the filter F3 with respect to the filter F1 is due to the higher concentration of the absorber Exciton P491. As another consequence of the high absorber concentration, the b*-value of the filter F3 is higher than that of the filter F1.

The filter F2 recovers a low value for the colorimetric parameter b*, thanks to the colour-balancing effect which is provided by the absorber Exciton ABS 584L with respect to the absorber Exciton P491. It also appears that the physiological effectiveness of the absorber Exciton ABS 584L in the melanopsin regeneration range is substantially similar to that of doubling the amount of the absorber Exciton P491.

In most preferred implementations, the ophthalmic element which is provided with light-filtering features according to the invention may be a smart element. In the frame of the present description, smart ophthalmic element denotes an ophthalmic element which is capable of switching between two optical states and maintaining each state, each state corresponding to a value for the element efficiency factor F which is distinct from the value relating to the other state. Switching of the element may be controlled or triggered by various control parameters, such as the activity, time in the day, ambient light intensity, etc.

But preferably, such smart ophthalmic element implementing the invention is electrically controlled. Light filters which can be varied in filtering capabilities are well known, for example based on cholesteric liquid crystals. A controller may be combined with the smart ophthalmic element for real-time controlling the current state of the element, and also controlling a switching to the other state. Criteria for triggering a switching may include:
- at least one feature of the light currently reaching the ophthalmic element, for example the light intensity. Possibly, state with minimum value for the efficiency factor may be controlled below a first level for the ambient light intensity, then an increasing value for the efficiency factor may be controlled when ambient light intensity increases, until saturation occurs at a second level for the ambient light intensity;
- a history related to a feature for the light which has reached the ophthalmic element during a time period. For example, one may use a time-integrated light amount which is comprised in the melanopsin absorption range, when the element is designed for efficiency with respect to melanopsin-based non-visual physiological effects;
- the age of the wearer of the element, since it is known that elder people are less sensitive to light components in the blue range. Then it may be suitable to adapt the filtering efficiency of the ophthalmic element so as to reduce blue light attenuation for elder people;
- behaviour data and/or lifestyle data of the wearer of the element. For example, switching of the ophthalmic element into a state for improving sleeping quality may be controlled at desired or predetermined hours with respect to activity or schedule of the subject;
- a control action which is entered by the wearer of the ophthalmic element. An input button or tactile area may be provided on the element for switching controlled by the wearer; and
- colour appearance preferred by the wearer. As an example, a wearer may appreciate warm colours, meaning that it is pleasant for him to have visual perception of his environment with low level blue light components. Then it is possible for him to access higher values for the efficiency factor F, for example for an ophthalmic element which is designed for stimulating melanopsin-based non-visual physiological effects.

Although the invention has been described in more details for melanopsin-based non-visual physiological effects, with colorimetric issues entailed by the location of the melanopsin absorption range within the visible range, it is clear that the efficiency factor F as introduced can be applied to any other non-visual physiological effect.

Also the invention has been described mainly for spectacle eyeglasses, including ametropia-correcting or solar protection eyeglasses, but it can be implemented for any other ophthalmic element, including contact lenses, goggles, eye protection masks, helmet windows, etc.

The invention claimed is:

1. A transparent ophthalmic element for stimulating at least one non-visual physiological effect, the element having a spectral filtering effect according to a spectral light transmittance T expressed as percentage values over the wavelength visible range [380 nm -780 nm], wherein:
   the element has an efficiency factor F that is greater than or equal to 30, said efficiency factor F is represented by the following equation:

$$F = 100 - \frac{\int_{380\,nm}^{780\,nm} E(\lambda) \cdot M(\lambda) \cdot T(\lambda) \cdot d\lambda}{\int_{380\,nm}^{780\,nm} E(\lambda) \cdot M(\lambda) \cdot d\lambda}$$

wherein:
   $\lambda$, is light wavelength within the visible range;
   $T(\lambda)$ is the transmittance value of the element at wavelength $\lambda$;
   $M(\lambda)$ is a value of the spectral sensitivity profile M of the non-visual physiological effect at wavelength $\lambda$; and
   $E(\lambda)$ is a value of the spectral distribution E of the light intensity at wavelength $\lambda$, corresponding to at least part of the light which enters into the wearer's eye without using the filter;
wherein the efficiency factor value is greater than or equal to K–b*, K being a coefficient greater than or equal to 1, and b* being a CIE Lab colorimetric parameter for the light transmitted through the element;
wherein the at least one non-visual physiological effect is stimulated by reducing a light amount which enters the wearer's eye and which is comprised within a spectral sensitivity range of melanopsin, and the spectral sensitivity profile M is a spectral sensitivity profile of melanopsin; and
wherein the ophthalmic element comprises a transparent matrix material, and also comprises a first absorber which is distributed within the transparent matrix material, wherein said first absorber has a first light-absorption maximum between 460 nm and 510 nm for a wavelength value of a light impinging on the ophthalmic element.

2. The transparent ophthalmic element according to claim 1, wherein the spectral intensity distribution E relates to daylight, an incandescent light source, an electroluminescent diode, a display backlight or a fluorescent light source.

3. The transparent ophthalmic element according to claim 1, wherein coefficient K equals 1.2 and b* is less than 84.

4. The transparent ophthalmic element according to claim 1, wherein the transmittance T of the element has a profile with at least two local-minimum zones and at least one local-maximum zone within the wavelength visible range, a first one of said local-minimum zones containing a local-minimum wavelength located within the melanopsin absorption wavelength range, and a second one of said local-minimum zones containing another local-minimum wavelength located outside the melanopsin absorption wavelength range, and the local-maximum zone being intermediate in wavelength between said first and second local-minimum zones.

5. The transparent ophthalmic element according to claim 4, wherein the second local-minimum zone overlaps at least part of a melanopsin regeneration spectral range, light with wavelength contained within said melanopsin regeneration spectral range stimulating a regeneration of melanopsin molecules after said melanopsin molecules have absorbed light with wavelength contained in the melanopsin absorption wavelength range.

6. The transparent ophthalmic element according to claim 1, wherein the first absorber has a first light-absorption maximum between 487 nm and 497 nm for the light wavelength with a full width at half maximum of less than 40 nm, when said first absorber is dissolved in methylene chloride.

7. The transparent ophthalmic element according to claim 1, further comprising a second absorber which is also distributed within the transparent matrix material, wherein said second absorber has a second light-absorption maximum between 550 nm and 630 nm for the wavelength value of the light impinging on the ophthalmic element.

8. The transparent ophthalmic element according to claim 7, wherein the second absorber has a second light-absorption maximum between 579 nm and 589 nm for light wavelength with a full width at half maximum of less than 30 nm, when said second absorber is dissolved in methylene chloride.

9. The transparent ophthalmic element according to claim 7, wherein the first absorber and the second absorber are each provided in an amount such that the efficiency factor F of the ophthalmic element is greater than 30 and b* is less than 10.

10. The transparent ophthalmic element according to claim 1, wherein the element remains in one of at least two states, each state corresponding to one value for the efficiency factor F which is distinct from the value relating to the other state, and wherein the element switches between both states.

11. The transparent ophthalmic element according to claim 10, further comprising a controller real-time controlling the current state of the element, and controlling a switching to the other state based on at least one of the following criteria:
    at least one feature of the light currently reaching the element;
    a history of at least one feature for the light which has reached the element during a time period;
    an age of the wearer of the element;
    behaviour data and/or lifestyle data of the wearer of the element; and
    at least one control action entered by the wearer of the element.

12. The transparent ophthalmic element according to claim 1, forming at least part of an eyeglass or at least part of an ophthalmic patch to be fitted on an eyeglass.

\* \* \* \* \*

UNITED STATES PATENT AND TRADEMARK OFFICE
CERTIFICATE OF CORRECTION

PATENT NO. : 11,137,625 B2  Page 1 of 1
APPLICATION NO. : 16/065270
DATED : October 5, 2021
INVENTOR(S) : Coralie Barrau and Montserrat Burgos It is certified that error appears in the above-identified patent and that said Letters Patent is hereby corrected as shown below:

In the Claims

Claim 1, Column 4, Line 40:
Delete "K–b*" and replace with -- K × b* --.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*